(12) United States Patent
Adams

(10) Patent No.: US 9,439,939 B2
(45) Date of Patent: Sep. 13, 2016

(54) HEAVY METALS DEFENSE

(71) Applicant: Webseed, Inc., Cody, WY (US)

(72) Inventor: Michael A. Adams, Tuscon, AZ (US)

(73) Assignee: WEBSEED, INC., Cody, WY (US)

( * ) Notice: Subject to any disclaimer, the term of this patent is extended or adjusted under 35 U.S.C. 154(b) by 0 days.

(21) Appl. No.: 14/667,754

(22) Filed: Mar. 25, 2015

(65) Prior Publication Data

US 2015/0273008 A1    Oct. 1, 2015

Related U.S. Application Data

(60) Provisional application No. 61/973,588, filed on Apr. 1, 2014.

(51) Int. Cl.

| A61K 36/87 | (2006.01) |
| A61K 36/05 | (2006.01) |
| A61K 36/04 | (2006.01) |
| A61K 36/06 | (2006.01) |
| A61K 35/748 | (2015.01) |
| A61K 35/08 | (2015.01) |
| A61K 9/14 | (2006.01) |
| A61K 9/48 | (2006.01) |

(52) U.S. Cl.
CPC .............. *A61K 36/87* (2013.01); *A61K 9/141* (2013.01); *A61K 9/4841* (2013.01); *A61K 35/08* (2013.01); *A61K 35/748* (2013.01); *A61K 36/05* (2013.01)

(58) Field of Classification Search
CPC ...... A61K 36/87; A61K 36/05; A61K 36/04; A61K 35/06
USPC ..................... 424/195.17, 611, 766
See application file for complete search history.

(56) References Cited

U.S. PATENT DOCUMENTS

| 4,192,756 A * | 3/1980 | Mondshine .............. C01D 3/26 252/383 |
| 8,257,694 B2 * | 9/2012 | Daikeler ................. A23L 1/034 424/195.15 |
| 2006/0121137 A1 * | 6/2006 | Hartle .................... A61K 36/87 424/766 |
| 2007/0082008 A1 * | 4/2007 | Harel .................... A23K 1/007 424/195.16 |

FOREIGN PATENT DOCUMENTS

| CN | 102018135 A | * | 4/2011 | |
| WO | WO 2005032268 A2 | * | 4/2005 | ........... A23K 1/1612 |

* cited by examiner

*Primary Examiner* — Chris R Tate
*Assistant Examiner* — Deborah Davis
(74) *Attorney, Agent, or Firm* — Neifeld IP Law, PC

(57) ABSTRACT

A dietary supplement comprising powdered ingredients: a) dehydrated seaweed: 40-60 wt. %, b) seawater extract: 20-40 wt. %, c) grape seed powder: 10-20 wt. %, d) *Chlorella*: 5-10 wt. %, e) *Spirulina*: 5-10 wt %, methods of making and using the composition.

20 Claims, No Drawings

HEAVY METALS DEFENSE

CROSS REFERENCE TO RELATED APPLICATIONS

This application claims benefit of Application No. 61/973,588, filed Apr. 1, 2014. The contents of Application No. 61/973,588 are hereby incorporated by reference in their entirety.

FIELD OF THE INVENTION

A dietary supplement having affinity for ionic heavy metals.

BACKGROUND OF THE INVENTION

Heavy Metals Defense (HMD) is a dietary supplement comprising five natural ingredients generally recognized as safe ("GRAS") by the FDA. In combination, they have the unique chemical property of demonstrating strong affinity for ionic heavy metals by an ion exchange mechanism.

This type of ion exchange behavior is analogous to that of "Prussian Blue," which is an FDA-approved drug for binding with cesium-137, a radioactive isotope. Prussian blue traps radioactive cesium and thallium in the intestines, and prevents these metals from being re-absorbed by the body. The radioactive materials then move through the intestines and are passed (excreted) in bowel movements. Because Prussian blue reduces the time that radioactive cesium and thallium stay in the body it helps to limit the amount of time that the body is exposed to radiation. (see http://www.bt.cdc.gov/radiation/prussianblue.asp)

Prussian blue works using a mechanism known as ion exchange. Cesium or thallium that have been absorbed into the body are removed by the liver and passed into the intestine and are then re-absorbed into the body (enterohepatic circulation). Prussian blue works by trapping thallium and cesium in the intestine, so that they can be passed out of the body in the stool rather than be re-absorbed. If persons are exposed to radioactive cesium, radioactive thallium, or non-radioactive thallium, taking Prussian Blue may reduce the risk of death and major illness from radiation or poisoning. (see http://www.fda.gov/Drugs/Emergencypreparedness/BioterrorismandDrugPreparedness/ucm130337.htm).

SUMMARY OF THE INVENTION

An object of the invention is to provide a dietary supplement composition, comprising:
powdered ingredients
a) dehydrated seaweed: 40-60 wt %
b) seawater extract: 20-40 wt. %
c) grape seed powder: 10-20 wt. %
d) *Chlorella:* 5-10 wt. %
e) *Spirulina:* 5-10 wt. %,
   wherein particle sizes for all particles can be from #40 mesh to #100 mesh.

Another object of the invention is to provide a method of producing a dietary supplement composition, comprising combining powdered ingredients as follows,
a) dehydrated seaweed: 40-60 wt. %
b) seawater extract: 20-40 wt. %
c) grape seed powder: 10-20 wt %
d) *Chlorella:* 5-10 wt %
e) *Spirulina:* 5-10 wt. %,
   wherein particle sizes for all particles can be from #40 mesh to #100 mesh.

Another object is to provide a method of causing heavy metals to be excreted from an animal, comprising feeding to an animal in need of fecal excretion of heavy metals a dietary supplement containing an effective amount of grape seed powder, wherein about 99% of particles in said grape seed powder are larger than 5 microns.

DETAILED DESCRIPTION OF THE INVENTION

HMD is made from: a) dehydrated seaweed, b) seawater extract, c) grape seed powder, d) *chlorella*, and e) *spirulina*. The finished product is provided as an encapsulated powder. The powder is slightly grayish white in color.

HMD is a dietary supplement comprising five natural ingredients and assembled for the purpose of allowing people to consume the capsules alongside herbs, foods or beverages which they believe may contain high levels of heavy metals such as lead, cadmium, arsenic and mercury. HMD exhibits active ion exchange which selectively binds to heavy metals, preventing them from being absorbed through intestinal walls during digestion. Most dietary substances show little or no selective affinity for heavy metals binding when subjected to an identical testing process. Only very few substances demonstrate a strong ion exchange potential for heavy metals.

It is believed that the formula of the invention works the same way as Prussian Blue, except that HMD is made from natural dietary substances, not a synthetic chemical. HMD is intended to be used as a dietary supplement, to be taken when someone consumes a product which is thought to contain worrisome levels of heavy metals, such as:
Chinese medicine herbs
Rice protein supplements
Tuna and other ocean fish
Sushi
Agricultural products grown in China During digestion the gastric acid found in human stomachs interacts with HMD ingredients, causing them to attain a high state of affinity for ionic heavy metals such as lead, cadmium, mercury, aluminum, etc. Heavy metals tend to carry positive charges such as Aluminum (+3), Lead (+2), etc. HMD carries a strong negative ionic charge, once activated, causing it to bind with lead, aluminum, cadmium, etc.

Once bound, HMD carries the toxic heavy metals with it through the entire digestive tract, ultimately transporting the heavy metals out of the body and preventing them from being reabsorbed through intestinal walls.

Heavy Metals Defense Ingredients Preparation

The following section describes the harvesting and preparation of each ingredient in the formula:

Dehydrated seaweed: Seaweed specimens are collected by swimmers from shallow coastal waters and stacked in a large washing container. They are washed to remove debris and salt water. After washing they are dried using a large commercial air dryer with a slow mixing agitation wheel in order to allow the seaweed sufficient exposure to air. Once fully dried, the seaweed specimens are ground to a power of approximately a #100 mesh size, producing a gray-white powder. This powder is packaged for use in manufacturing.

Seawater extract: A saturated salt (brine) area of seawater is identified, usually at very low depth. The water is extracted by means of a long pump, then mixed with dolomitic limestone $(CaMg(Co_3)_2)$ to precipitate solids. The mixture is heated to high temperature, driving off the carbon dioxide and leaving "calcined dolime," a seawater extract. This solid material is ground to approximately #100 mesh particle size.

Grape seed powder: Fresh grapes are washed, then pressed through a commercial grape press machine to extract the grape juice. The remaining mass consists of grape peels and grape seeds. This mass is heated to high temperature then rinsed to eliminate the grape peels, leaving only grape seeds. The seeds are dried, then ground into a fine powder of approximately #60 mesh.

*Chlorella*: Strains of the single-celled algae known as *Chlorella vulgaris* are grown in large vats of water and fed sufficient nutrients to support their growth to maturity. Once fully grown, *chlorella* is harvested out of the water by means of large filters which separate the *chlorella* alga from the water in which they were grown. This green mass is rinsed with fresh water, flash dried on a conveyor belt, then agitated by powerful sonic blasts in order to disrupt their cell walls and provide improved bioavailability. Finally, this green mass is powdered to a relatively large mesh size of around #40 mesh.

*Spirulina*: Spirulina pacifica is a strain of edible blue-green algae which can be grown in large outdoor pools which combine fresh water with deep ocean water that enriches the *spirulina* with minerals. Once fully grown, the *spirulina* is harvested from the water by means of large filters giving a green mass which is rinsed with fresh water, flash dried on a conveyor belt, then ground to a relatively large mesh size of around #40 mesh.

Particle sizes of the above ingredient are specifically chosen to avoid passing through intestinal walls (99% of particles are >5 microns in diameter).

Carriers and processing aids may be used to obtain satisfactory flow and packaging characteristics. These excipients can include antitacking agents such as talc, stearic acid, magnesium stearate and colloidal silicon dioxide and the like, surfactants such as polysorbates and potassium lauryl sulphate, fillers such as precipitated calcium carbonate, polishing agents such as beeswax and the like. All these excipients can be used at levels well known to the persons skilled in the art In general the product is manufactured in an environment free of airborne metals in order to preserve the ion exchange "potential" of the raw materials.

Preferred Ratio Ranges of the Heavy Metals Defense Formula

Dehydrated seaweed: 40-60 wt. %
Seawater extract: 20-40 wt. %
Grape seed powder: 10-20 wt. %
*Chlorella*: 5-10 wt. %
*Spirulina*: 5-10 wt. %,
wherein particle sizes for all particles can be from #40 mesh to #100 mesh.

Encapsulation Process

The HMD powder is encapsulated and packaged using traditional powder encapsulation methods which are customarily used in dietary supplements manufacturing. Specifically, raw materials are weighed, apportioned and blended using a large commercial blender. The resulting blended power is deposited into the encapsulation machine. Empty vegetarian capsules are also deposited into the machine. The machine opens each capsule and fills each capsule with approximately 400 mg of power, then firmly closes each capsule. Capsules are then counted by machine and dropped into supplement bottles.

Desiccants are dropped into the bottles to absorb moisture. A capper affixes a cap with a special seal containing both a sealant and a thin metallic element which is sensitive to induction. An induction machine exposes the lid of the bottle to a brief electric current sufficient to create heat to seal the top of the bottle, under the lid. A shrink bander machine affixes a shrink band around the neck of the bottle. A heat tunnel shrinks the shrink band, creating a tight seal. A labeler affixes the product label. The bottle is then boxed into cases for distribution.

Laboratory Protocol for Validation of HMD

One gram of HMD formula is placed in a polypropylene vial (vial #1). A second vial is set aside for control testing (vial #2), with no HMD placed in it (zero grains).

To each vial, 20 ml of synthetic gastric acid is added. This acid has a pH of around 1.0 and is made of deionized (DI) water, hydrochloric acid (HCl), sodium chloride and potassium chloride, all in ratios that mimic typical human gastric acid.

A 2 ml liquid "spike" of heavy metals is then added to both vials using precise volumetric liquid handling via pipette. This spike contains a known concentration of lead, cadmium, arsenic, mercury, copper, aluminum, uranium and zinc. The spike is custom formulated from a competent "external standards" formulator and is ICP-MS verified and traceable to NIST standards.

Both vials are then subjected to simulated digestion for a period of 8 hours. This digestion is conducted at human body temperature with agitation designed to mimic digestion in the human stomach. After digestion, both vials are filtered through a 2-micron filter to remove any solid particles which would not be small enough to pass through intestinal walls. 5 ml of the remaining liquid is extracted from each vial and placed in a fresh, new vial in preparation for acid digestion.

5 ml of Nitric Acid ($HNO_3$) is added to each vial. Both vials are digested via HotBlock digestion, at a temperature of 100° C. for a period of two hours. The vials are then removed from the HotBlock and allowed to cool. Both vials are then normalized to 50 ml total volume using a blank acid normalization liquid made of DI water, 2% $HNO_3$, 0.5% HCl and 200 ppb Au (for mercury stabilization).

These vials are placed in an auto-sampler connected to an ICP-MS atomic spectroscopy instrument which has been calibrated by the manufacturer and validated by field technicians. The instrument runs a multi-element custom calibration process followed by a mid-range calibration check. Calibration blanks are also run before and after the samples in order to further confirm the accuracy of the instrument. External calibration solutions are prepared and run at 0 ppb, 1 ppb, 10 ppb, 100 ppb and 1000 ppb concentrations. An internal standard is mixed with the sample intake liquid for analysis accuracy.

Unknown samples are then run and concentrations of analytes are calculated from the calibration runs, as is customary in all ICP-MS laboratory operations. Element concentrations found in vial #2 provide the "baseline concentration" of elements in the total 22 ml of synthetic gastric acid. Element concentrations found in vial #1 are then compared to the baseline, element by element. The difference in the two concentrations is the reduction of elemental concentrations caused by the HMD formula. This number is calculated element by element.

In one embodiment of the invention tested using the above protocol, significant reductions in targeted elements ranging from about 82 percent to 100 percent were achieved, as follows:

Al: 99%
Cu: 96.3%
As: 92.9%
Cd: 99.9%
Cs: 28.6%
Hg: 100%
Pb: 100%
U: 82.1%
Zn: 99.5%

In one embodiment of the invention the dietary supplement contains the following powdered ingredients:
a) dehydrated seaweed, #100 mesh, 50 wt. %
b) seawater extract, #100 mesh, 30 wt. %
c) grape seed powder, #60 mesh, 15 wt. %
d) *Chlorella,* #40 mesh, 7.5 wt. %
e) *Spirulina,* #40 mesh, 7.5 wt. %, It will be apparent to those skilled in the art that variations and modifications of the invention can be made without departing from the spirit and scope of the teachings above. It is intended that the specification and examples be considered as exemplary only and are not restrictive.

The invention claimed is:

1. A dietary supplement composition, consisting of:
powdered ingredients encapsulated in a water-soluble vegetable capsule and consisting of:
a) dehydrated seaweed particles: #100 mesh, 50 wt. %
b) calcined dolime particles, as seawater extract: #100 mesh, 20 wt. %
c) grape seed powder particles: #60 mesh, 15 wt. %
d) *Chlorella vulgaris* particles: #40 mesh, 5-10 wt. %
e) *Spirulina pacifica* particles: #40 mesh, 5-10 wt. % and
f) a remainder consisting of excipient particles selected from the group consisting of anticaking agent, surfactant, filler, and polishing agent; the anticaking agent being selected from the group consisting of talc, stearic acid, magnesium stearate, and colloidal silicon dioxide; the surfactant being selected from the group consisting of polysorbate and potassium lauryl sulfate; the filler being precipitated calcium carbonate; the polishing agent being beeswax;
wherein 99% of all particles in the composition are larger than 5 microns in diameter.

2. The composition of claim 1, wherein the *Chlorella vulgaris* particles are 5 wt. %.
3. The composition of claim 1, wherein the *Chlorella vulgaris* particles are 7.5 wt. %.
4. The composition of claim 1, wherein the *Chlorella vulgaris* particles are 10 wt. %.
5. The composition of claim 1, wherein the *Spirulina pacifica* particles are 5 wt. %.
6. The composition of claim 1, wherein the *Spirulina pacifica* particles are 7.5 wt. %.
7. The composition of claim 1, wherein the *Spirulina pacifica* particles are 10 wt. %.
8. The composition of claim 1, wherein the excipient particles are anticaking agent.
9. The composition of claim 1, wherein the anticaking agent is talc.
10. The composition of claim 1, wherein the anticaking agent is stearic acid.
11. The composition of claim 1, wherein the anticaking agent is magnesium stearate.
12. The composition of claim 1, wherein the anticaking agent is colloidal silicon dioxide.
13. The composition of claim 1, wherein the excipient particles are surfactant.
14. The composition of claim 1, wherein the surfactant is polysorbate.
15. The composition of claim 1, wherein the surfactant is potassium lauryl sulfate.
16. The composition of claim 1, wherein the excipient particles are precipitated calcium carbonate.
17. The composition of claim 1, wherein the excipient particles are beeswax.
18. A method of producing the dietary supplement composition of claim 1, consisting of:
combining the powdered ingredients, and encapsulating in the capsule, to produce the composition.
19. The method of claim 18, wherein the composition is produced in an environment free of airborne heavy metals.
20. A method of causing heavy metals to be excreted from an animal, consisting of:
feeding to an animal in need of fecal excretion of heavy metals the composition of claim 1.

* * * * *